(12) United States Patent  (10) Patent No.: US 8,277,446 B2
Heard  (45) Date of Patent: Oct. 2, 2012

(54) ELECTROSURGICAL TISSUE SEALER AND CUTTER

(75) Inventor: David N. Heard, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 698 days.

(21) Appl. No.: 12/429,533

(22) Filed: Apr. 24, 2009

(65) Prior Publication Data

US 2010/0274244 A1   Oct. 28, 2010

(51) Int. Cl.
*A61B 18/18* (2006.01)

(52) U.S. Cl. .......................................................... 606/51

(58) Field of Classification Search ............... 606/45–52
See application file for complete search history.

(56) References Cited

U.S. PATENT DOCUMENTS

| | | | |
|---|---|---|---|
| 4,770,173 A | 9/1988 | Feucht et al. | |
| 5,122,137 A | 6/1992 | Lennox | |
| 5,443,463 A | 8/1995 | Stern et al. | |
| 5,536,267 A | 7/1996 | Edwards et al. | |
| 5,540,722 A | 7/1996 | Clare et al. | |
| 5,700,261 A | 12/1997 | Brinkerhoff | |
| 5,833,690 A * | 11/1998 | Yates et al. | 606/52 |
| 5,843,019 A | 12/1998 | Eggers et al. | |
| 5,865,361 A | 2/1999 | Milliman | |
| 6,083,223 A * | 7/2000 | Baker | 606/52 |
| 6,152,923 A | 11/2000 | Ryan | |
| 6,454,758 B1 | 9/2002 | Thompson et al. | |
| 6,500,176 B1 * | 12/2002 | Truckai et al. | 606/51 |
| 6,527,767 B2 | 3/2003 | Wang et al. | |
| 6,656,177 B2 | 12/2003 | Truckai et al. | |
| 6,773,435 B2 * | 8/2004 | Schulze et al. | 606/51 |
| 7,011,657 B2 * | 3/2006 | Truckai et al. | 606/51 |
| 7,083,618 B2 | 8/2006 | Couture et al. | |
| 7,250,048 B2 | 7/2007 | Francischelli et al. | |
| 7,303,557 B2 | 12/2007 | Wham et al. | |
| 7,473,253 B2 * | 1/2009 | Dycus et al. | 606/51 |
| 7,727,231 B2 * | 6/2010 | Swanson | 606/41 |
| 7,955,331 B2 * | 6/2011 | Truckai et al. | 606/51 |
| 7,981,113 B2 * | 7/2011 | Truckai et al. | 606/49 |
| 2002/0115997 A1 * | 8/2002 | Truckai et al. | 606/51 |
| 2002/0177849 A1 * | 11/2002 | Schulze et al. | 606/50 |

(Continued)

FOREIGN PATENT DOCUMENTS

CA    2520413    3/2007

(Continued)

OTHER PUBLICATIONS

International Search Report EP 10160870 dated Aug. 9, 2010.

*Primary Examiner* — Kevin C Sirmons
*Assistant Examiner* — Andrew Gilbert

(57) ABSTRACT

A surgical instrument comprises an end effector including a pair of jaw members configured to move with respect to one another between an open configuration and a closed configuration for clamping tissue. At least one jaw member includes an elongate cam slot extending in a longitudinal direction over a substantial a length a tissue clamping surface of the at least one jaw member. A plurality of electrically isolated, and longitudinally spaced electrodes is supported by the tissue clamping surface and is configured to deliver electrosurgical energy to tissue. A reciprocating member engages the elongate cam slot and is extendable to a sealing position with respect to each of the electrodes to define a predetermined gap distance between a particular electrode and an opposing tissue clamping surface.

16 Claims, 10 Drawing Sheets

U.S. PATENT DOCUMENTS

| | | | |
|---|---|---|---|
| 2002/0188294 A1* | 12/2002 | Couture et al. | 606/51 |
| 2003/0195513 A1* | 10/2003 | Truckai et al. | 606/51 |
| 2003/0199870 A1* | 10/2003 | Truckai et al. | 606/51 |
| 2005/0171535 A1 | 8/2005 | Truckai | |
| 2006/0069388 A1 | 3/2006 | Truckai et al. | |
| 2008/0045947 A1* | 2/2008 | Johnson et al. | 606/51 |
| 2008/0277449 A1 | 11/2008 | Marczyk | |
| 2009/0076506 A1* | 3/2009 | Baker | 606/51 |
| 2009/0076534 A1 | 3/2009 | Shelton, IV | |

FOREIGN PATENT DOCUMENTS

| | | |
|---|---|---|
| EP | 2206474 | 7/2010 |
| WO | WO9507662 | 3/1995 |
| WO | WO2009039179 | 3/2009 |

\* cited by examiner

ELECTROSURGICAL TISSUE SEALER AND CUTTER

BACKGROUND

1. Technical Field

The present disclosure relates to an apparatus and related method for electrosurgically sealing tissue. In particular, the disclosure relates to sealing tissue with a series of discrete electrode segments spaced over a targeted region of the tissue.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping surfaces of the jaws. The electrodes are charged to opposite electrical potentials such that an electrosurgical current may be selectively transferred through tissue grasped between the electrodes. To effect a proper seal, particularly in relatively large vessels, two predominant mechanical parameters should be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined.

Certain surgical procedures may be performed more quickly and accurately with an electrosurgical forceps having relatively longer electrodes than one having shorter electrodes. To this end, electrosurgical forceps have become available with electrodes 60 mm in length or more. Longer electrodes, however, may tend to present difficulties in maintaining a uniform pressure and gap distance, and thus, creating an effective seal along the entire length of the jaws may prove difficult. For example, where a pair of jaws is pivotally coupled by a pivot pin at a proximal region of the jaws, the effects of manufacturing tolerances may be amplified according to a longitudinal distance from the pivot pin. Tissue captured at a distal region of the jaws may thus encounter greater gap distances and lower clamping forces than tissue captured at a proximal region near the pivot pin. This non-uniformity may make it difficult to adequately control the necessary mechanical parameters to generate an effective seal along the entire length of the electrodes.

Also, longer electrodes may tend to have greater power requirements than shorter electrodes. Current up to 5 amps may be drawn by longer electrodes, which is near a limit set for some commercially available electrosurgical generators.

SUMMARY

The present disclosure describes a surgical instrument for sealing tissue. The instrument comprises an end effector including a pair of jaw members having a opposing tissue clamping surfaces, wherein at least one of the jaw members configured to move with respect to the other jaw member to move the end effector between an open configuration for receiving tissue and a closed configuration for clamping tissue between the opposing clamping surfaces. The at least one jaw member includes an elongate cam slot extending longitudinally along the at least one jaw member over a substantial a length of the tissue clamping surfaces. A plurality of electrically isolated electrodes is supported by at least one of the tissue clamping surfaces of the jaw members, and each of the plurality of electrodes is longitudinally spaced along the at least one tissue clamping surface and is configured to deliver electrosurgical energy to the tissue. A reciprocating member is extendable through the elongate cam slot to a longitudinal sealing position with respect to each of the electrodes, wherein when the reciprocating member is in the sealing position with respect to a particular electrode the reciprocating member defines a predetermined gap distance between the particular electrode and the opposing clamping surface.

The surgical instrument may also include an interruption mechanism to interrupt advancement of the reciprocating member at each of the longitudinal sealing positions. The interruption mechanism may includes a handle movable with respect to a grip member, wherein the reciprocating member is operatively coupled to the movable handle such that the reciprocating member is advanced upon approximation of the movable handle with the grip member and advancement of the reciprocating member is interrupted upon separation of the movable handle from the grip member. Alternatively, the interruption mechanism may include a motor and a controller, wherein the motor is operatively associated with the reciprocating member to advance the reciprocating member upon activation of the motor and interrupt advancement upon deactivation of the motor, and wherein the controller is operatively associated with the motor to activate and deactivate the motor. A sensor array in electrical communication with the controller may be adapted to detect the position of the reciprocating member with respect to at least one sealing position.

The surgical instrument may further comprise a controller for providing electrical energy to a particular electrode while maintaining other electrodes in an electrically inactive state. A sensor array in electrical communication with the controller may be adapted to detect a characteristic of the tissue indicative of a completed electrosurgical treatment. The sensor array may include at least one of a temperature sensor, an impedance sensor and an optical sensor.

The reciprocating member may include a blade for transecting tissue. The reciprocating member may include a cam driver configured to engage the elongate cam slot and the blade may be disposed proximally with respect to a cam driver. The blade may be disposed sufficiently proximally with respect to the cam driver such that when the reciprocating member is in a sealing position associated with a particular electrode, the blade is disposed proximally of the particular electrode.

The reciprocating member may generally exhibit an I-beam geometry including a pair of opposed flanges connected by an intermediate web. One of the pair of opposed flanges may engage the elongate cam slot defined in one of the jaw members and the other of the pair of opposed flanged may engage a second cam slot defined in the other of the jaw members. The elongate cam slot may include a proximal portion curved such that advancement of the reciprocating member therethrough urges the end effector to the closed configuration.

The plurality of electrodes may include a plurality of electrode sets. Each electrode set may include at least two electrodes of opposite polarity supported by respective clamping surfaces such that the electrodes of opposite polarity may cooperate to induce an electrosurgical current to flow through tissue positioned between the clamping surfaces.

According to another aspect of the disclosure, a surgical instrument comprises an end effector including a pair of jaw members. At least one of the jaw members is configured to move with respect to the other jaw member to move the end effector between an open configuration for receiving tissue and a closed configuration for clamping tissue between a pair of opposed clamping surfaces supported by the jaw members. A plurality of electrically isolated electrodes is supported by at least one of the clamping surfaces of the jaw members. Each of the plurality of electrodes is longitudinally spaced along the at least one clamping surface and is configured to deliver electrosurgical energy to the tissue. A reciprocating member includes a blade, the reciprocating member extendable to a longitudinal sealing position with respect to each of the electrodes, wherein when the reciprocating member is in the sealing position with respect to a particular electrode the blade is disposed immediately proximally of the particular electrode. An interruption mechanism is provided to interrupt advancement of the reciprocating member at each of the sealing positions.

According to another aspect of the disclosure, a method for electrosurgically treating tissue comprises providing an instrument including a plurality of electrically isolated electrodes spaced longitudinally along at least one tissue clamping surface of one of a pair of jaw members. The instrument also includes a reciprocating member longitudinally movable to a sealing position with respect to each of the plurality of electrodes. The reciprocating member defines a predetermined gap distance between a particular electrode an opposing tissue clamping surface jaw member when in the sealing position with respect to the particular electrode. The method also comprises positioning tissue between the opposing tissue clamping surfaces such that at least a first proximal electrode and a second distal electrode of the plurality of electrodes contacts the tissue, and advancing the reciprocating member to the sealing position with respect to the first proximal electrode to clamp the tissue between the first proximal electrode and the opposing tissue clamping surface at the predetermined gap distance. Advancement of the reciprocating member is interrupted to maintain the reciprocating member at the sealing position with respect to the first proximal electrode while providing electrosurgical energy to the first proximal electrode and maintaining the second distal electrode in an electrically inactive state. The reciprocating member is further advanced to the sealing position with respect to the second distal electrode to clamp the tissue between the second distal electrode and the opposing tissue clamping surface at the predetermined gap distance, and advancement of the reciprocating member is again interrupted to maintain the reciprocating member at the sealing position with respect to the second distal electrode while providing electrosurgical energy to the second distal electrode and maintaining the first proximal electrode in an electrically inactive state.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
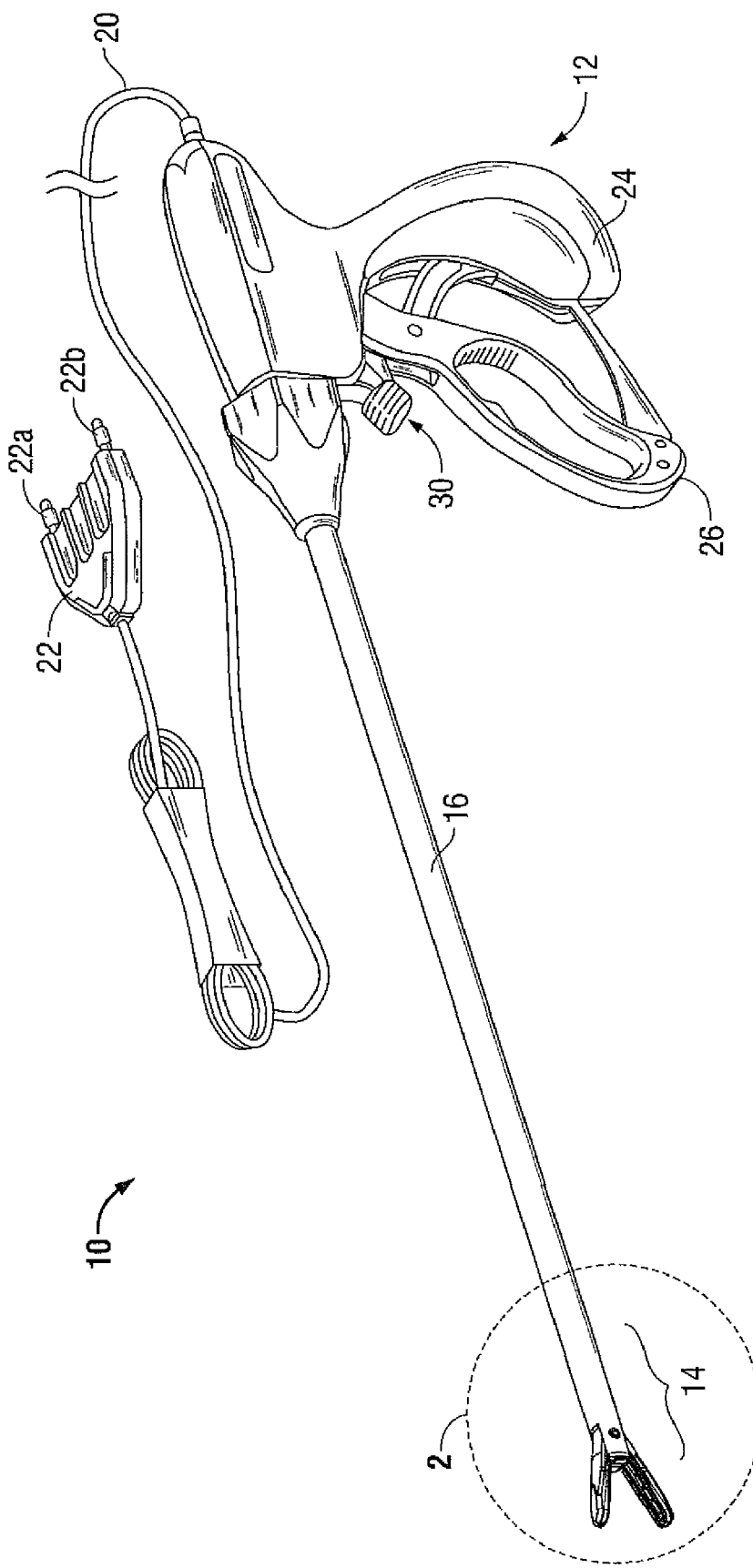
FIG. 1 is a perspective view of a surgical instrument in accordance with the present disclosure.

Referring initially to FIG. 1, an embodiment of an electrosurgical instrument is depicted generally as 10. The instrument 10 includes a handle assembly 12 for remotely controlling an end effector 14 through an elongate shaft 16. Although this configuration is typically associated with instruments for use in laparoscopic or endoscopic surgical procedures, various aspects of the present disclosure may be practiced in connection with traditional open procedures as well as endoluminal procedures.

Handle assembly 12 is coupled to an electrosurgical cable 20, which may be used to connect the instrument 10 to a source of electrosurgical energy. The cable 20 extends to connector 22 including prong members 22a and 22b, which are dimensioned to mechanically and electrically connect the instrument 10 to an electrosurgical generator (not shown). Each of the two prong members 22a and 22b may be associated with an opposite electrical potential (supplied by the generator) such that bipolar energy may be conducted through the cable 20, and to the end effector 14.

To control the end effector 14, the handle assembly 12 includes a stationary handle 24 and movable handle 26. The movable handle 26 may be separated and approximated relative to the stationary handle 24 to respectively open and close the end effector 14. A trigger 30 is also disposed on the handle assembly 12, and is operable to initiate and terminate the delivery of electrosurgical energy through the end effector 14.

Figure 2:
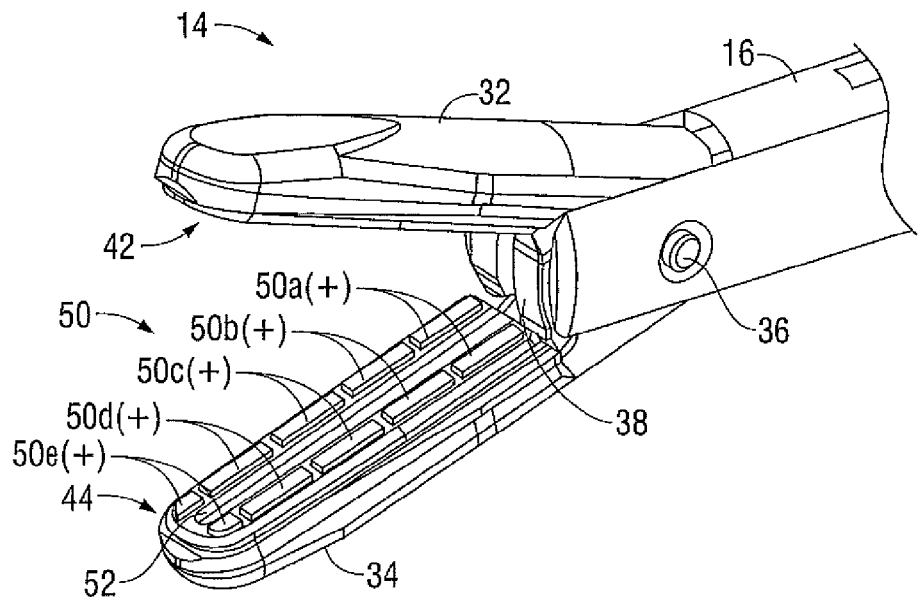
FIG. 2 is an enlarged, perspective view of a distal end of the instrument of FIG. 1 depicting an end effector in an open configuration.
Figure 6:
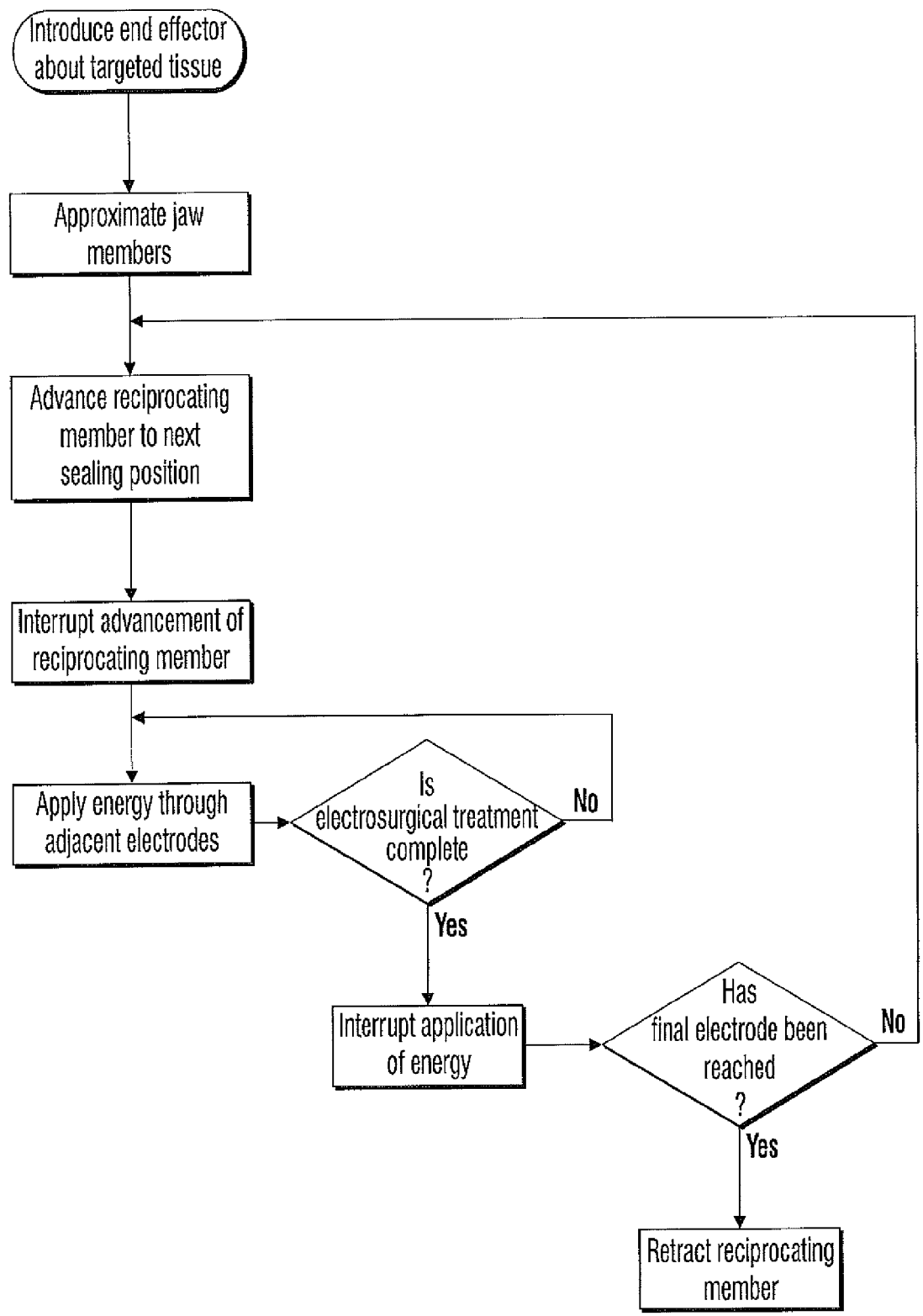
FIG. 6 is a flow diagram describing a process for sealing the targeted tissue of FIG. 6 using the instrument of FIG. 1.

Referring now to FIG. 2, end effector 14 is depicted in an open configuration. Upper and lower jaw members 32 and 34 are separated from one another such that tissue may be received therebetween. The jaw members 32, 34 are each pivotally coupled to the elongate shaft 16 by a respective pivot pin 36. The lower jaw member 34 includes a proximal flange 38 extending into a bifurcated distal end of the elongate shaft 16 and engaging the pivot pin 36. The upper jaw member 32 is similarly coupled to the elongate shaft 16 such that the two jaw members 32, 34 are pivotally movable relative to one another. End effector 14 is thus movable between the open configuration depicted in FIG. 2 and a closed configuration depicted in FIG. 6 wherein the jaw members 32, 34 are closer together. Other constructions are also envisioned including constructions in which only one jaw member moves.

The upper and lower jaw members 32, 34 define clamping surfaces 42 and 44. Tissue positioned between the clamping surfaces 42 and 44 will encounter a clamping force applied by the jaw members 32, 34 when the end effector 14 is moved to the closed configuration. Each of the clamping surfaces 42, 44 carries a plurality of discrete electrode segments thereon collectively identified as 50. The electrode segments 50 are arranged in pairs longitudinally spaced along the clamping surfaces 42, 44. For example, a first pair of electrodes 50a(+) occupies a first a proximal region of the clamping surface 44 of the lower jaw member 34. Four additional pairs of electrodes 50b(+), 50c(+), 50d(+) and 50e(+) are spaced longitudinally in successively distal regions of the clamping surface 44. Electrode pairs 50a(−), 50b(−), 50c(−), 50d(−) and 50e(−) (FIG. 3) occupy corresponding regions of the clamping surface 42 of the upper jaw member 32. The corresponding electrode pairs, 50a(+) and 50a(−), for example, may be charged to opposite polarities such that they cooperate to induce an electrosurgical current to flow through tissue positioned between the clamping surfaces 42 and 44. Although the clamping surfaces 42, 44 are each depicted as including five electrode pairs, any number of longitudinally spaced electrodes is contemplated.

A knife channel 52 extends longitudinally through each of the jaw members 32 and 34. The knife channel 52 permits a reciprocating member 54 (FIG. 3) to traverse the clamping surfaces 42, 44 to sever tissue positioned therebetween. Since each electrode of the electrode pairs, 50a(+) for example, includes one electrode 50 disposed on each lateral side of the knife channel 52, an accurate cut may be generated between regions of sealed tissue.

Figure 3:
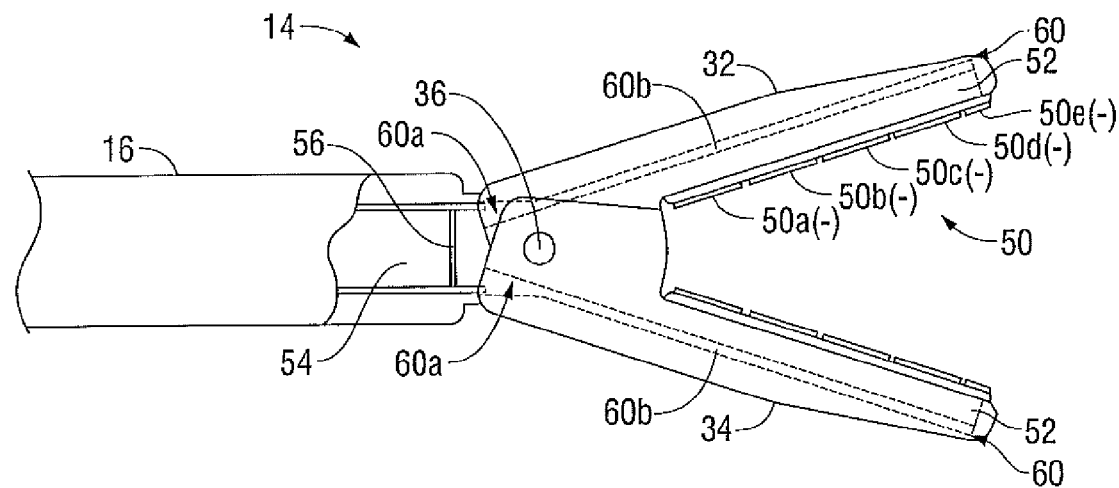
FIG. 3 is a broken, side view of the end effector of FIG. 2 depicting a reciprocating member in a retracted position.

Referring now to FIG. 3, reciprocating member 54 is slidably disposed within the elongate shaft 16. The reciprocating member 54 may be advanced distally into the knife channel 52 of the jaw members 32, 34. Since each jaw member 32 and 34 is coupled to the elongate shaft 16 by a separate pivot pin 36, the reciprocating member 54 may pass between the pivot pins 36 as the reciprocating member 54 is advanced distally. The reciprocating member 54 includes a sharpened blade 56 at a forward edge that permits the reciprocating member 54 to transect tissue as the reciprocating member 54 is advanced through the knife channel 52.

The knife channel 52 includes a pair of elongate cam slots 60 extending longitudinally through each of the jaw members 32, 34. The elongate cam slots 60 each include a proximal region 60a for engaging the reciprocating member 54 to move the end effector 14 between the open and closed configurations. The proximal regions 60a are curved such that advancement of the reciprocating member 54 therethrough in a distal direction causes the jaw members 32, 34 to pivot toward one another about the pivot pins 36. Further advancement of the reciprocating member 54 causes the reciprocating member 54 to engage distal regions 60b of the cam slots 60. The distal regions 60b are generally flat and allow the reciprocating member 54 to define a gap distance "G" between the electrodes 50 as described below with reference to FIG. 5.

Figure 4:
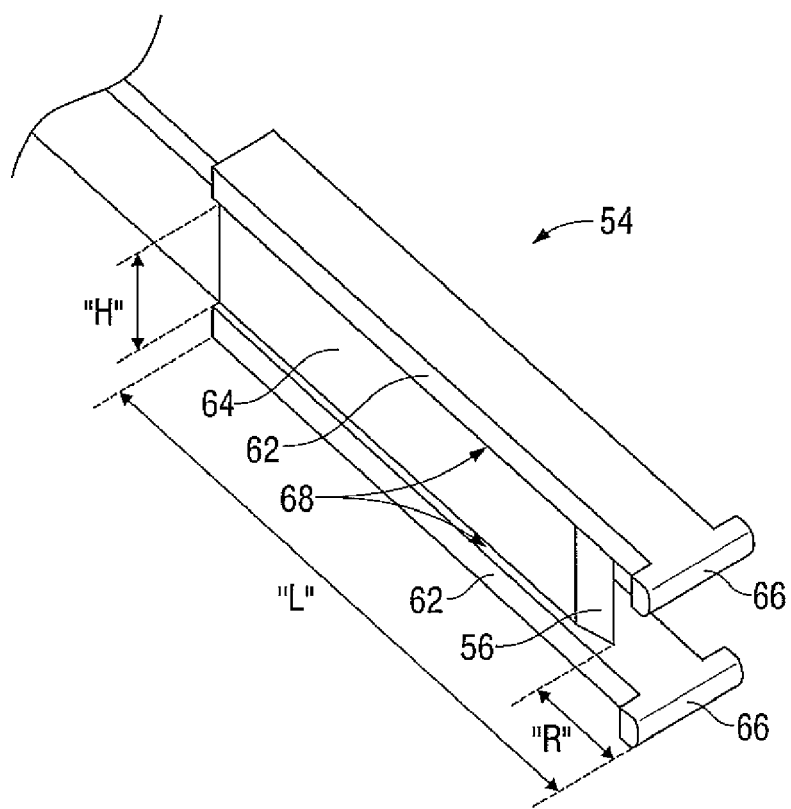
FIG. 4 is a partial, perspective view of the reciprocating member of FIG. 3.
Figure 5:
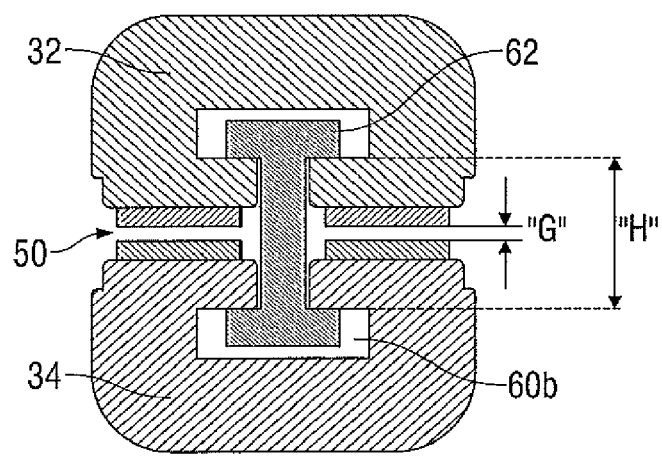
FIG. 5 is a cross-sectional view of the end effector of FIG. 2 in a closed configuration.

Referring now to FIGS. 4 and 5, the geometry of a distal portion of the reciprocating member 54 generally resembles an I-beam having a pair of opposed flanges 62 connected by an intermediate web 64. The flanges 62 each include a forward cam driver 66 at a distal end, and a cam engagement surface 68 extending laterally from the web 64. The cam engagement surfaces 68 have a longitudinal length "L" approximating a length of the cam slots 60, permitting the reciprocating member 54 to engage the jaw members 32, 34 substantially over a length of the clamping surfaces 42, 44. A forward edge of the web 64 forming the sharpened blade 56 is recessed a distance "R" from the forward cam drivers 66. This recess permits the reciprocating member 54 to engage the cam slots 60 at a distal location with respect to blade 56.

The cam engagement surfaces 68 oppose one another and are separated by a predetermined distance "H." When the reciprocating member 54 is advanced into the jaw members 32, 34, the engagement surfaces 68 engage the distal regions 60b of the cam slots 60 to define a gap distance "G" between electrodes 50. The gap distance "G" is typically between about 0.001 and about 0.006 inches for sealing many tissue types, although greater gap distances "G" may be suitable for some tissue types of for other electrosurgical processes.

Figure 7:
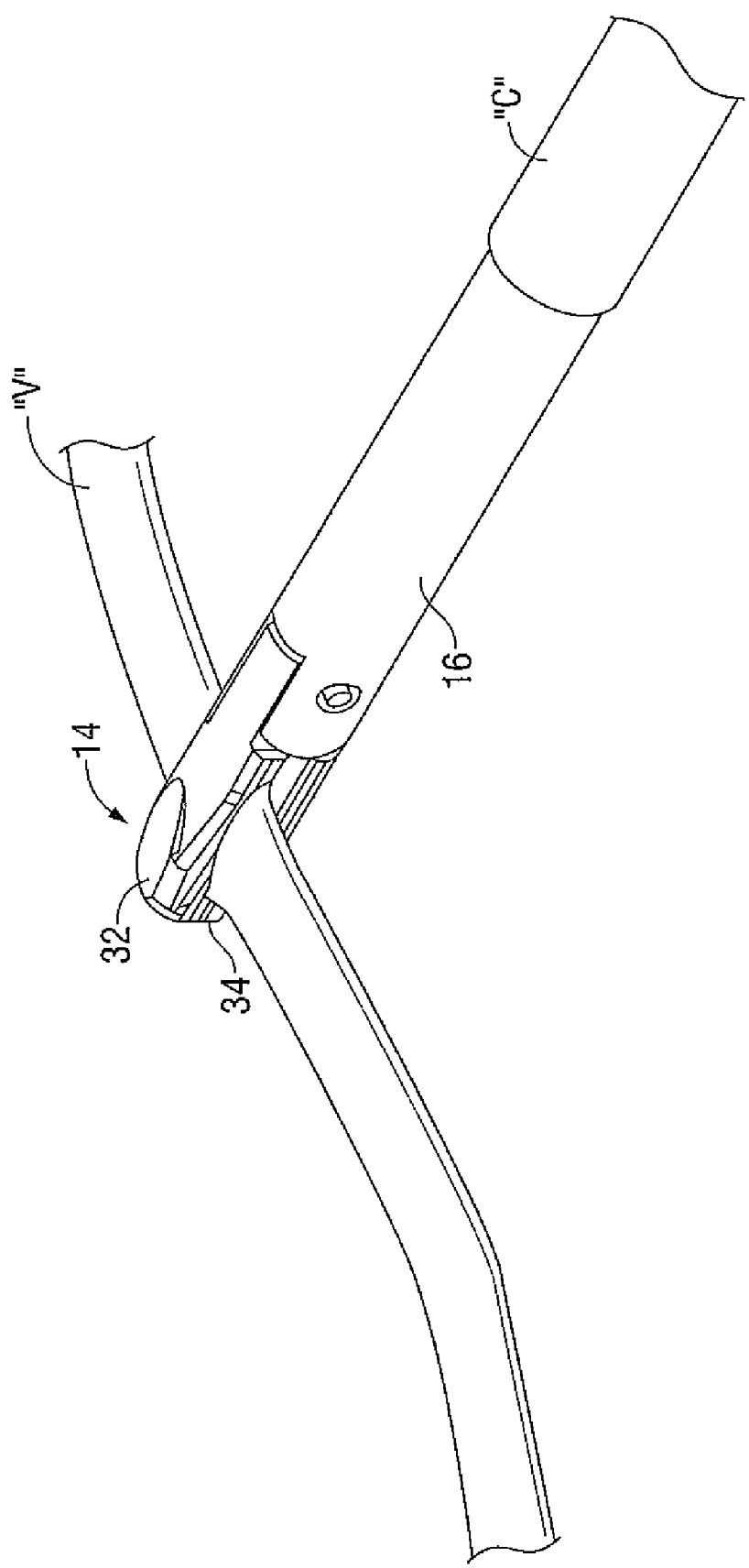
FIG. 7 is a partial, perspective view of targeted tissue at a surgical site clamped by the end effector of FIG. 2.

Referring now to FIGS. 6 through 8C, a process for sealing and dividing tissue such as vessel "v" includes the steps of introducing the end effector 14 into a body cavity and clamping the vessel "V." The end effector 14 may be introduced into the body cavity through a cannula "C" as depicted in FIG. 7, and the jaw members 32, 34 may be approximated to contact the vessel "V." The jaw members 32, 34 may be approximated by advancing the forward cam drivers 66 of the reciprocating member 54 over the proximal regions 60a of the cam slots 60 as discussed above.

Figure 8A:
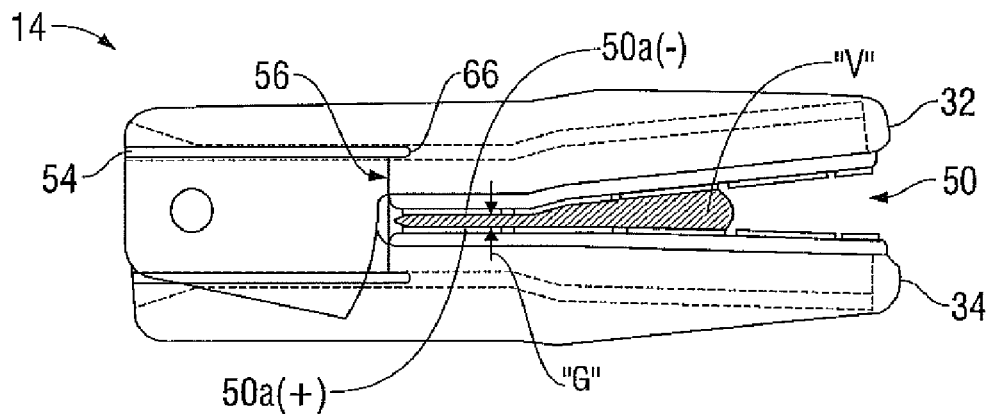
FIGS. 8A through 8C are schematic views of the end effector of FIG. 6 in various stages of the process described in FIG. 7.

Next the reciprocating member 54 is advanced to a first sealing position as indicated in FIG. 8A. With the reciprocating member 54 in the first sealing position, the forward cam drivers 66 extend sufficiently distally to define an appropriate gap distance "G" between a first set of electrodes 50a(+) and 50a(−). A separation distance greater than the gap distance "G" may be develop between electrodes 50 disposed distally with respect to the first set of electrodes 50a(+) and 50a(−). Such larger separation distances may occur in part due to relatively high reactionary forces applied by the vessel "V" and any inherent flexibility in the jaw members 32, 34. The flexibility of the jaw members 32, 34 as illustrated in FIGS. 8A through 8C is exaggerated for clarity.

The first sealing position depicted in FIG. 8A is also characterized by the immediately proximal location of the forward blade 56 with respect to the vessel "V" and the first set of electrodes 50a(+) and 50a(−). This arrangement helps to ensure that no unsealed tissue is cut. Advancement of the reciprocating member 54 is interrupted to maintain the reciprocating member 54 at the first sealing position.

Next, electrosurgical energy is applied to the first set of electrodes 50a(+) and 50a( ) for an appropriate amount of time to effect tissue sealing. The remainder of the electrodes 50 may remain electrically inactive while an electrosurgical current is induced through the vessel "V" in the vicinity of the first set of electrodes 50a(+) and 50a(−). Thus, tissue in the immediate vicinity of the reciprocating member 54 may be sealed while tissue positioned between more distal electrodes 50 remains untreated. Once tissue sealing has been effected between the first set of electrodes 50a(+) and 50a(−), the application of electrosurgical energy is interrupted.

Figure 8B:
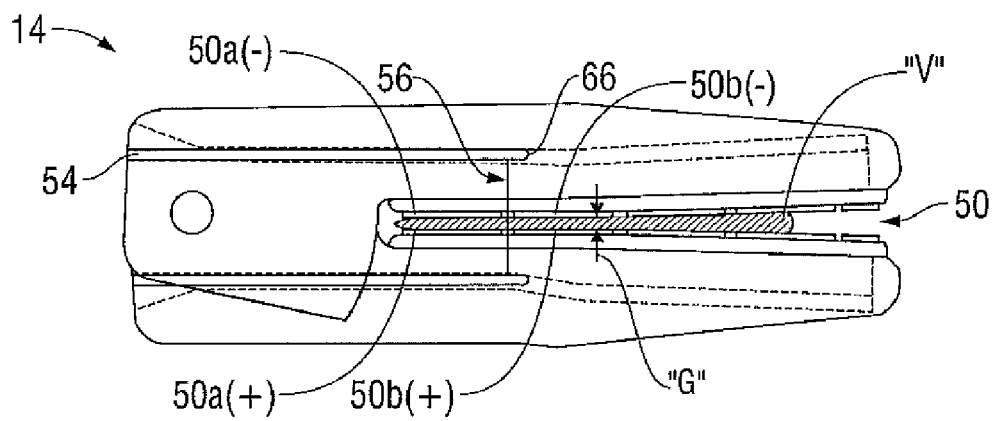
Figure 8C:
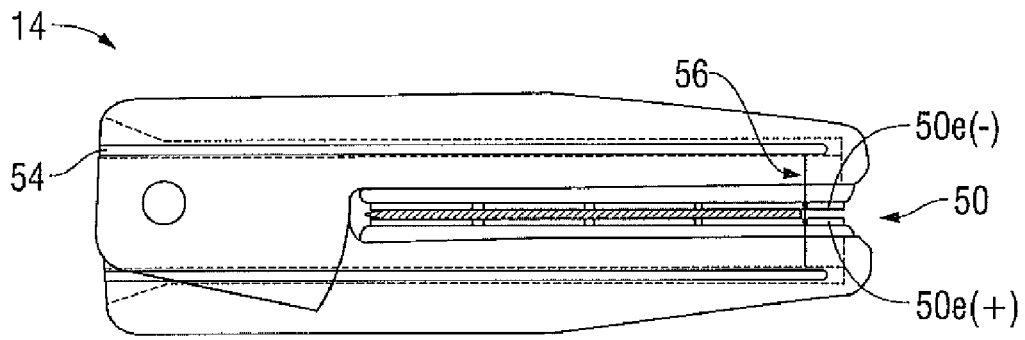

Next, the reciprocating member 54 is advanced to a subsequent sealing position as indicated in FIG. 8B. As the reciprocating member 54 is advanced, the forward blade 56 transects the tissue positioned between the first set of electrodes 50a(+) and 50a (−) while the forward cam drivers 66 establish the appropriate gap distance "G" between a the subsequent set of electrodes 50b(+) and 50b(−). Advancement of the reciprocating member 54 is again interrupted such that the reciprocating member 54 is maintained in the subsequent sealing position. The application of electrosurgical energy may be repeated for the subsequent set of electrodes 50b(+) and 50b(−) while the remainder of the electrodes 50 remain electrically inactive.

The steps of advancing the reciprocating member 54, interrupting the advancement of the reciprocating member 54, and applying electrosurgical energy to a selected set of electrodes 50 may be repeated until the reciprocating member reaches a final or distal most set of electrodes 50e(+) and 50e(−) as depicted in FIG. 8C. In this position, all of the tissue has been sealed and transected by the forward blade 56. Thus, the reciprocating member 54 may be retracted, releasing the vessel "V" from the end effector 14. Alternatively, and particularly in instances where tissue spills out beyond the end effector 14, an electrosurgical current may be applied to the final set of electrodes 50e(+) and 50e(−) to effect sealing therebetween. Retracting the reciprocating member 54 at this point allows a portion of sealed tissue to remain unsevered by the forward blade 56. The sealed and unsevered tissue may facilitate further surgical action on the tissue.

Several features may be incorporated into a surgical instrument to facilitate various aspects of the procedure. For example, indicators may be provided to alert an operator of an instrument status, or that a particular step of the procedure is complete and that the subsequent steps may be performed.

Figure 9:
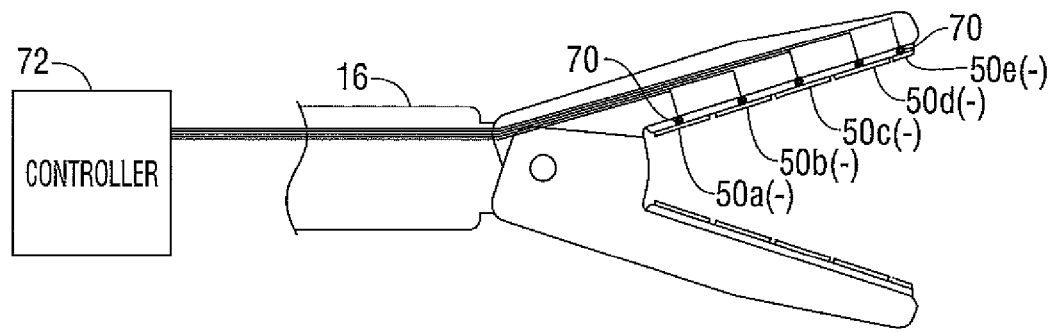
FIG. 9 is a schematic view of a sensor array associated with the end effector of FIG. 2.

As depicted in FIG. 9, an indicator may be associated with an array of temperature sensors 70. Each temperature sensor 70 is positioned appropriately to detect a temperature of tissue positioned adjacent one of the electrode pairs, 50a(−) for example. The sensors 70 are electrically coupled to controller 72 through the elongate shaft 16. The controller may be positioned within the handle assembly 12 (FIG. 1), or alternatively within the electrosurgical generator, which provides the electrosurgical energy to the electrodes 50. The controller 72 provides an indication to an operator that a particular tissue temperature has been achieved. For example, as electrosurgical energy is applied to the first set of electrodes 50a(+) and 50a(−), tissue positioned therebetween may tend to heat up to a particular temperature associated with properly sealed tissue. When this temperature is achieved, the controller may emit an audible tone, provide a flashing light or otherwise alert the operator that sealing has been completed. The operator may interrupt the application of electrosurgical energy be releasing the trigger 30 (FIG. 1), or alternatively the controller 70 may be configured to provide a signal to the electrosurgical generator to automatically discontinue the delivery of electrosurgical energy. Sensors 70 may also include an impedance sensor and/or an optical sensor to detect a characteristic of effectively sealed tissue.

Figure 10:
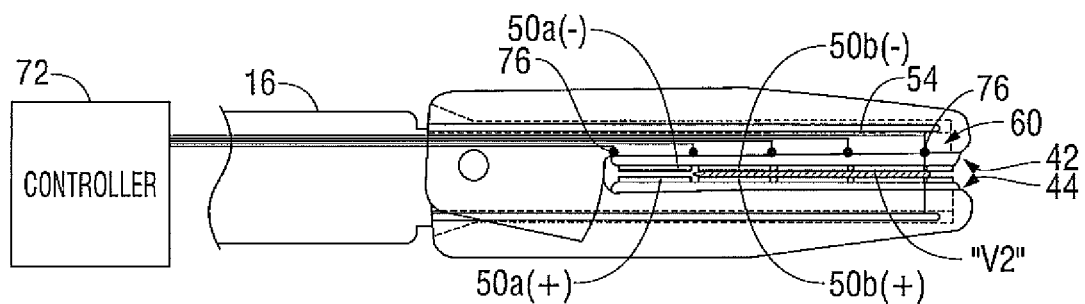
FIG. 10 is a schematic view of an alternate embodiment of a sensor array.

As depicted in FIG. 10, an array of position sensors 76 may be alternatively or additionally provided. Each position sensor 76 is configured and positioned to detect a position of the reciprocating member 54 within the elongate cam slots 60. The sensors 76 are also electrically coupled to the controller 72. Thus, the controller 72 may provide an indicator to the operator that the reciprocating member 54 has been advanced to a sealing position.

Each of the electrodes 50 may also be electrically coupled to the controller 72 to detect the presence of tissue positioned between a set of electrodes 50. For example, when a vessel such as "V2" (FIG. 10) is positioned between the clamping surfaces 42, 44 some of the electrodes 50 may contact tissue, and others may not. The controller 72 may be configured to send an electrical signal to a test electrode 50a(+), for example, and monitor an opposite electrode 50a(−) to determine whether tissue is positioned between the electrodes 50a(+), 50a(−). A signal detected at a tissue contacting electrode 50b(−), for example, will be distinguishable from a signal detected at an electrode 50a(−) that does not contact tissue. For the vessel "V2," the controller 72 may provide an indicator to the operator that electrosurgical energy does not need to be applied to the first set of electrodes 50a(+), 50a(−), and that the reciprocating member 54 may be advanced directly to the subsequent set of electrodes 50b(+), 50b(−).

Figure 11A:
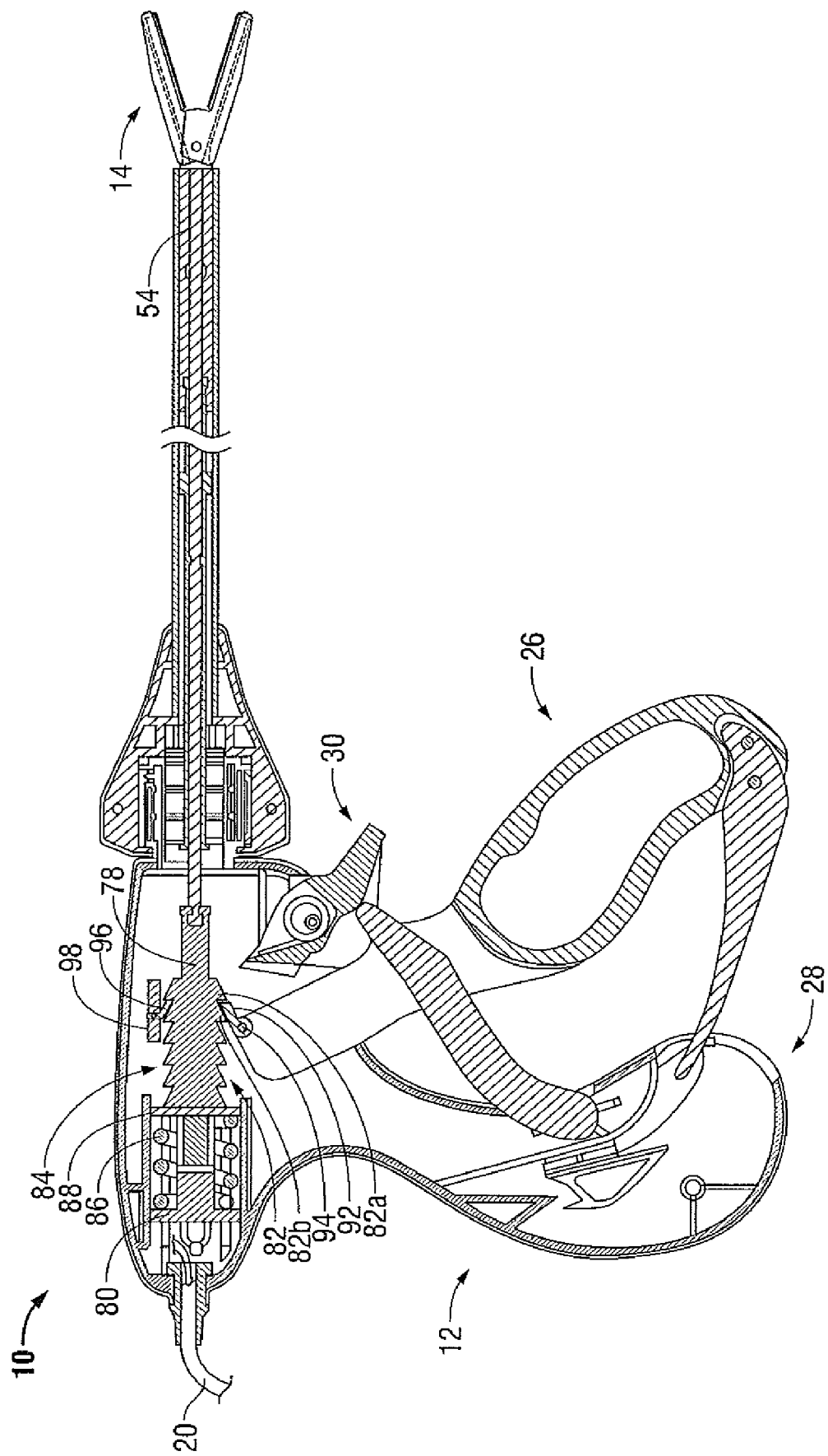
FIG. 11A is a cross sectional view of the instrument of FIG. 1 depicting an actuation mechanism for manually effecting the process of FIG. 7.
Figure 11B:
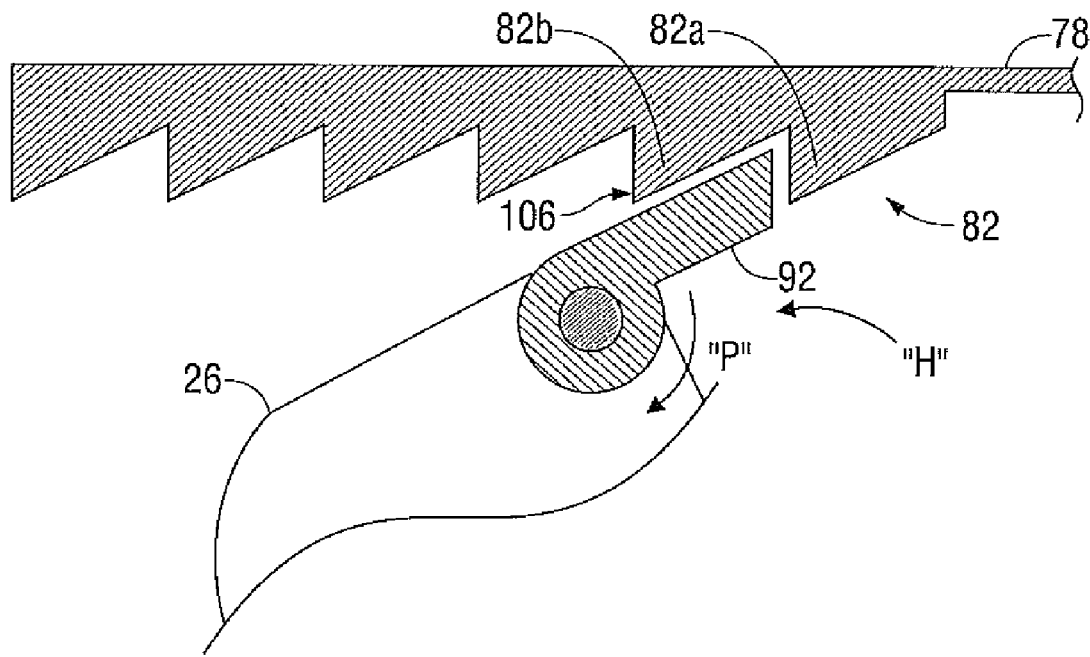
FIG. 11B is a close-up view of a drive mechanism depicted in FIG. 11A.
Figure 11C:
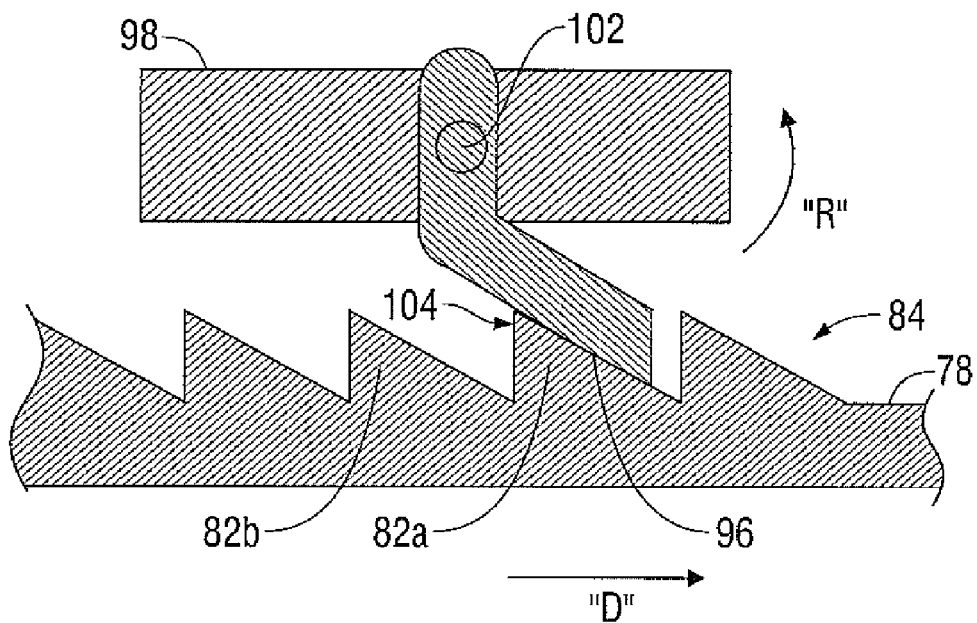
FIG. 11C is a close up view of a locking mechanism depicted in FIG. 11A.

Referring now to FIGS. 11A, 11B and 11C, a mechanism for appropriately advancing and interrupting the reciprocating member 54 is housed within handle assembly 12. The reciprocating member 54 is coupled to a drive shaft 78 such that the longitudinal motion of the drive shaft 78 is transferred to the reciprocating member 54. The drive shaft 78 includes a flange 80 at a proximal end, and a driving rack 82 and a locking rack 84 extending longitudinally along the shaft 78. The drive shaft 78 is biased in a proximal direction by compression spring 86 captured between a fixed housing member 88 and the flange 80.

A driving pawl 92 is pivotally mounted to movable handle 26 about a pivot pin 94. The driving pawl 92 is pivotally biased toward the driving rack 82 by a biasing member such as a torsion spring (not shown). Similarly, a locking pawl 96 is pivotally mounted to a stationary housing member 98 about a pivot pin 102. The locking pawl 96 is pivotally biased toward the locking rack 84 by a biasing member such as a torsion spring (not show).

In use, the movable handle 26 may be approximated with the stationary grip member 28 to drive the driving pawl 92 in a distal direction. The driving pawl 92 bears on a drive tooth 82a of the driving rack 82 to drive the drive shaft 78 in a distal direction, which drives the reciprocating member 54 in a distal direction. Thus, the movable handle 26 may initially be approximated with the stationary grip member 28 to move the end effector 14 from an open configuration to a closed configuration as discussed above with reference to FIG. 3.

As the drive shaft 78 moves distally (see arrow "D" in FIG. 11B), a tooth 84a of the locking rack 84 presses on the locking pawl 96. The locking pawl 96 pivots in the direction of arrow "R" against the bias of the biasing member until the tooth 84a has moved sufficiently to disengage the locking pawl 96. The biasing member then causes the locking pawl 96 to pivot back toward the locking rack 84 such that the locking pawl 96 engages a locking face 104 of the tooth 84a. Engagement of the locking pawl 96 with the locking face 104 maintains a longitudinal position of the drive shaft 78, and thus the reciprocating member 54.

With the longitudinal position of the drive shaft 78 maintained, separation of the movable handle 26 from the stationary grip member 28 causes a motion of the driving pawl 92 in the direction of arrow "H" (FIG. 11B) relative to the driving rack 82. The driving pawl 92 pivots against the bias of the biasing member in the direction of arrow "P" as it moves proximally past a second drive tooth 82b. Once the driving pawl 92 is moved proximally beyond the second drive tooth 82b, the biasing member causes the driving pawl 92 to pivot back toward the drive rack 82 such that the driving pawl 92 engages a driving face 106 of the second drive tooth 82b.

Once the driving face 106 is engaged, the movable handle 26 may again be approximated with the stationary grip member 28 to advance further advance the reciprocating member the drive shaft 78 and the reciprocating member 54.

The mechanism depicted in FIG. 11A may thus be used to advance the reciprocating member 54 to each subsequent sealing position by repeatedly approximating and separating the movable handle 26 relative to the stationary grip 28. Advancement of the reciprocating member 54 is automatically interrupted at each sealing position as the movable handle 26 must be separated from the grip 28 to effect further advancement. When the reciprocating member 54 is fully advanced, a release (not shown) may be activated to pivot the driving pawl 92 and the locking pawl 96 away from the drive shaft 78. This will permit retraction of the reciprocating member 54 under the bias of the compression spring 86.

Figure 12:
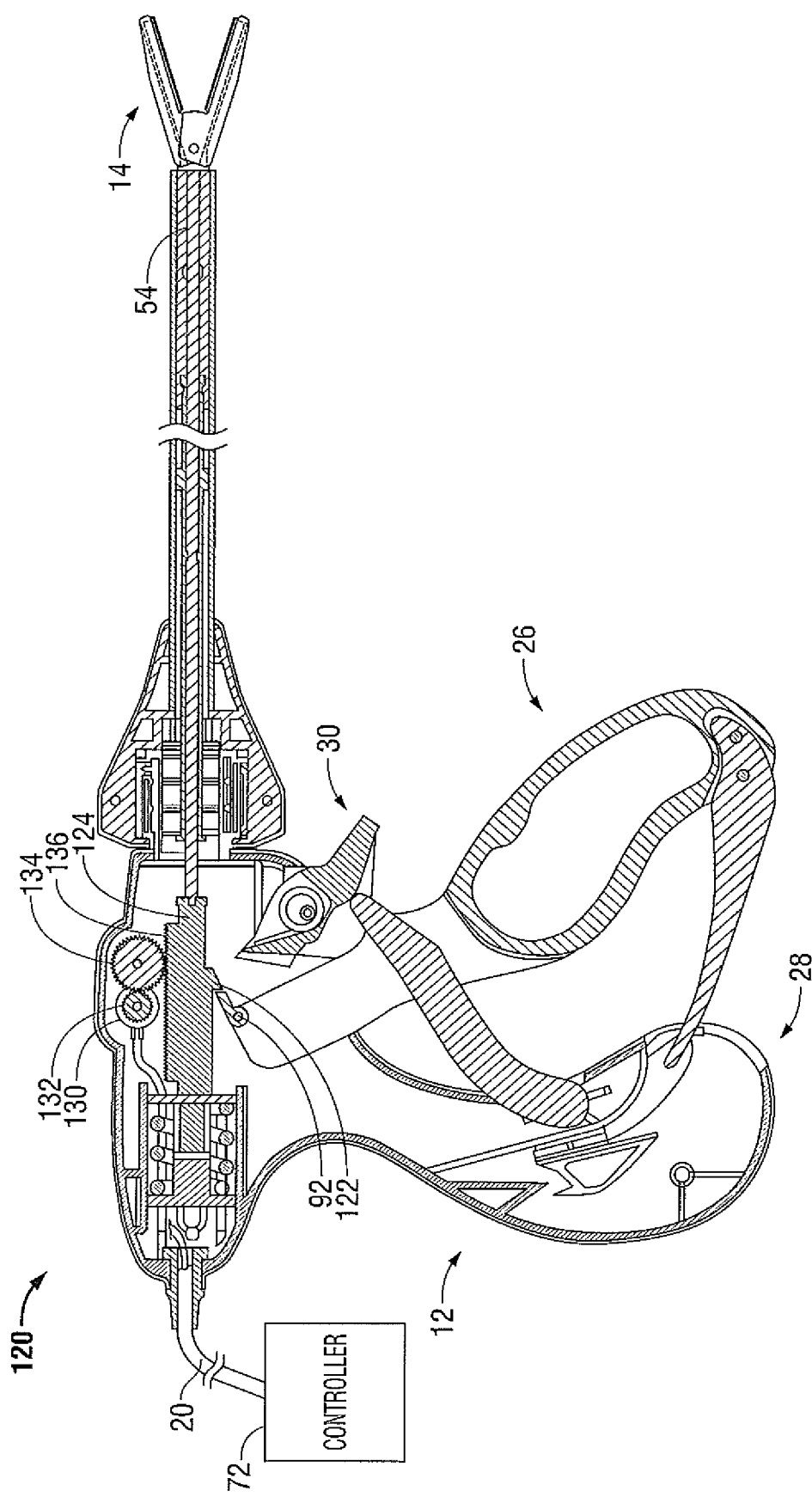
FIG. 12 is a cross sectional view of an alternate embodiment of an actuation mechanism for partially automating the process of FIG. 7.

Referring now to FIG. 12, an instrument 120 includes an actuation mechanism for partially automating the advancement of the reciprocating member 54. Instrument 120 includes a movable handle 26, which is movable relative to a stationary grip member 28 similar to the instrument 10 discussed above with reference to FIG. 11A. A driving pawl 92 is mounted to the movable handle 26 and engages a drive wedge 122 protruding from a drive shaft 124. The drive shaft 124 is coupled to the reciprocating member 54 such that longitudinal motion of the drive shaft 124 is transferred to the reciprocating member 54. Thus, the movable handle 26 may initially be approximated with the stationary grip member 28 to move the end effector 14 from an open configuration to a closed configuration as discussed above with reference to FIG. 3.

Thereafter, a motor 130 may be activated to drive the reciprocating member 54. The motor 130 is coupled to a clutch 132, which drives a pinion gear 134. The pinion gear 134, in turn drives a toothed rack 136 of the drive shaft 124.

The motor 130 is coupled to the controller 72 such that the motor 130 may receive instructions therefrom. The controller 72 may be configured to receive instructions from an operator as when to advance or interrupt motion of the reciprocating member 54. Alternatively, the controller 72 may include an algorithm to receive information from the electrodes 50 and sensors 70, 76 (FIGS. 9 and 10) to determine an appropriate time to advance and interrupt motion of the reciprocating member 54.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   an end effector including a pair of jaw members having opposing tissue clamping surfaces, at least one of the jaw members configured to move with respect to the other jaw member to move the end effector between an open configuration for receiving tissue and a closed configuration for clamping tissue between the opposing tissue clamping surfaces, the at least one jaw member including an elongate cam slot extending longitudinally along the at least one jaw member over a substantial a length of the tissue clamping surfaces;
   a plurality of electrically isolated electrodes supported by at least one of the tissue clamping surfaces of one of the jaw members, each of the plurality of electrodes longitudinally spaced along the at least one tissue clamping surface and configured to deliver electrosurgical energy to tissue; and
   a reciprocating member extendable through the elongate cam slot to a longitudinal sealing position with respect to each of the electrodes, wherein when the reciprocating member is in the sealing position with respect to a particular electrode, the reciprocating member defines a predetermined gap distance between the particular electrode and the opposing tissue clamping surface; and
   an interruption mechanism to interrupt advancement of the reciprocating member at each of the longitudinal sealing positions.

2. The surgical instrument according to claim 1, wherein the interruption mechanism includes a handle movable with respect to a grip member, wherein the reciprocating member is operatively coupled to the movable handle such that the reciprocating member is advanced upon approximation of the movable handle with the grip member and advancement of the reciprocating member is interrupted upon separation of the movable handle from the grip member.

3. The surgical instrument according to claim 1, wherein the interruption mechanism includes a motor and a controller, the motor operatively associated with the reciprocating member to advance the reciprocating member upon activation of the motor and interrupt advancement upon deactivation of the motor, the controller operatively associated with the motor to activate and deactivate the motor.

4. The surgical instrument according to claim 3, further comprising a sensor array in electrical communication with the controller, the sensor array adapted to detect the position of the reciprocating member with respect to at least one longitudinal sealing position.

5. The surgical instrument according to claim 1, further comprising a controller for providing electrical energy to a particular electrode while maintaining other electrodes in an electrically inactive state.

6. The surgical instrument according to claim 5, further comprising a sensor array in electrical communication with the controller, the sensor array adapted to detect a characteristic of the tissue indicative of a completed electrosurgical treatment.

7. The surgical instrument according to claim 6, wherein the sensor array includes at least one of a temperature sensor, an impedance sensor and an optical sensor.

8. The surgical instrument according to claim 1, wherein the reciprocating member includes a blade for transecting tissue.

9. The surgical instrument according to claim 8, wherein the reciprocating member includes a cam driver configured to engage the elongate cam slot and the blade is disposed proximally with respect to a cam driver.

10. The surgical instrument according to claim 9, wherein the blade is disposed sufficiently proximally with respect to the cam driver such that when the reciprocating member is in a sealing position associated with a particular electrode, the blade is disposed proximally of the particular electrode.

11. The surgical instrument according to claim 1, wherein the reciprocating member generally exhibits an I-beam geometry including a pair of opposed flanges connected by an intermediate web.

12. The surgical instrument according to claim 11, wherein one of the pair of opposed flanges engages the elongate cam slot defined in one of the jaw members and the other of the pair of opposed flanged engages a second cam slot defined in the other of the jaw members.

13. The surgical instrument according to claim 1, wherein the elongate cam slot includes a proximal portion curved such that advancement of the reciprocating member therethrough urges the end effector to the closed configuration.

14. The surgical instrument according to claim 1, wherein the plurality of electrodes includes a plurality of electrode sets, each electrode set including at least two electrodes of opposite polarity supported respective tissue clamping surfaces such that the electrodes of opposite polarity may cooperate to induce an electrosurgical current to flow through tissue positioned between the tissue clamping surfaces.

15. A surgical instrument comprising:
    an end effector including a pair of jaw members having opposing tissue clamping surfaces, at least one of the jaw members configured to move with respect to the other jaw member to move the end effector between an open configuration for receiving tissue and a closed configuration for clamping tissue between the opposing tissue clamping surfaces;
    a plurality of electrically isolated electrodes supported by at least one of the tissue clamping surfaces of one of the jaw members, each of the plurality of electrodes longitudinally spaced along the at least one clamping surface and configured to deliver electrosurgical energy the tissue;
    a reciprocating member including a blade, the reciprocating member extendable to a longitudinal sealing position with respect to each of the electrodes, wherein when the reciprocating member is in the sealing position with respect to a particular electrode the forward blade is disposed immediately proximally of the particular electrode; and
    an interruption mechanism configured to interrupt advancement of the reciprocating member at each of the sealing positions.

16. A method for electrosurgically treating tissue, the method comprising the steps of:
    providing an instrument including a plurality of electrically isolated electrodes being spaced longitudinally along at least one of a pair of tissue clamping surfaces of a pair of jaw members, the instrument also including a reciprocating member longitudinally movable to a sealing position with respect to each of the plurality of electrodes;
    positioning tissue between the opposing clamping surfaces such that at least a first proximal electrode and a second distal electrode of the plurality of electrodes contacts the tissue;
    advancing the reciprocating member to the sealing position with respect to the first proximal electrode to clamp the tissue between the first proximal electrode and the opposing tissue clamping surface at a predetermined gap distance;
    interrupting advancement of the reciprocating member to maintain the reciprocating member at the sealing position with respect to the first proximal electrode while providing electrosurgical energy to the first proximal electrode and maintaining the second distal electrode in an electrically inactive state;
    further advancing the reciprocating member to the sealing position with respect to the second distal electrode to clamp the tissue between the second distal electrode and the opposing tissue clamping surface at the predetermined gap distance; and
    interrupting advancement of the reciprocating member to maintain the reciprocating member at the sealing position with respect to the second distal electrode while providing electrosurgical energy to the second distal electrode and maintaining the first proximal electrode in an electrically inactive state.

* * * * *